United States Patent [19]

Osborne et al.

[11] Patent Number: 5,741,478
[45] Date of Patent: Apr. 21, 1998

[54] PREPARATION OF HOLLOW MICROCAPSULES BY SPRAY-DRYING AN AQUEOUS SOLUTION OF A WALL-FORMING MATERIAL AND A WATER-MISCIBLE SOLVENT

[75] Inventors: Nicholas Osborne, Colwick; Andrew Derek Sutton, Ruddington; Richard Alan Johnson, West Bridgford, all of United Kingdom

[73] Assignee: Andaris Limited, Nottingham, United Kingdom

[21] Appl. No.: 676,344

[22] PCT Filed: Nov. 15, 1995

[86] PCT No.: PCT/GB95/02673

§ 371 Date: Jul. 19, 1996

§ 102(e) Date: Jul. 19, 1996

[87] PCT Pub. No.: WO96/15814

PCT Pub. Date: May 30, 1996

[30] Foreign Application Priority Data

Nov. 19, 1994 [GB] United Kingdom .................. 9423419

[51] Int. Cl.$^6$ .............. A61K 49/04; A61K 9/14; B01F 3/00
[52] U.S. Cl. .......... 424/9.52; 424/489; 424/491; 252/314; 252/363.5
[58] Field of Search ............... 424/9.52, 9.51, 424/9.5, 489, 491; 128/662.02; 252/314, 363.5

[56] References Cited

U.S. PATENT DOCUMENTS

| | | | |
|---|---|---|---|
| 2,797,201 | 6/1957 | Veatch et al. | 260/2.5 |
| 3,501,419 | 3/1970 | Bridgeford | 260/2.5 |
| 3,781,230 | 12/1973 | Vassiliades et al. | 260/2.5 B |
| 3,937,668 | 2/1976 | Zolle | 252/316 |
| 3,960,583 | 6/1976 | Netting et al. | 106/122 |
| 4,089,800 | 5/1978 | Temple | 252/316 |
| 4,102,806 | 7/1978 | Kondo et al. | 252/316 |
| 4,107,288 | 8/1978 | Oppenheim et al. | 424/22 |
| 4,127,622 | 11/1978 | Watanabe et al. | 264/13 |
| 4,147,767 | 4/1979 | Yapel | 424/22 |
| 4,173,488 | 11/1979 | Vassiliades et al. | 106/213 |
| 4,247,406 | 1/1981 | Widder et al. | 252/62.53 |
| 4,276,885 | 7/1981 | Tickner et al. | 128/660 |
| 4,316,391 | 2/1982 | Tickner | 73/861.25 |
| 4,349,530 | 9/1982 | Royer | 424/19 |
| 4,357,259 | 11/1982 | Senyei et al. | 252/316 |
| 4,420,442 | 12/1983 | Sands | 264/13 |
| 4,442,843 | 4/1984 | Rasor et al. | 128/660 |
| 4,466,442 | 8/1984 | Hilmann et al. | 128/653 |
| 4,718,433 | 1/1988 | Feinstein | 128/660 |
| 4,774,958 | 10/1988 | Feinstein | 128/660.01 |
| 4,808,408 | 2/1989 | Baker et al. | 424/408 |
| 4,844,882 | 7/1989 | Widder et al. | 424/9 |
| 4,900,540 | 2/1990 | Ryan et al. | 424/9 |
| 4,957,656 | 9/1990 | Cerny et al. | 252/311 |
| 4,960,351 | 10/1990 | Kendall, Jr. et al. | 425/6 |
| 4,968,562 | 11/1990 | Delgado | 428/402 |
| 4,981,625 | 1/1991 | Rhim et al. | 264/13 |
| 5,137,928 | 8/1992 | Erbel et al. | 521/56 |
| 5,147,631 | 9/1992 | Glajch et al. | 424/9 |
| 5,190,982 | 3/1993 | Erbel et al. | 521/56 |
| 5,196,183 | 3/1993 | Yudelson et al. | 424/9 |
| 5,205,287 | 4/1993 | Erbel et al. | 128/632 |
| 5,215,680 | 6/1993 | D'Arrigo | 252/307 |
| 5,271,928 | 12/1993 | Schneider et al. | 424/9 |

(List continued on next page.)

FOREIGN PATENT DOCUMENTS

| | | |
|---|---|---|
| A-80297/91 | 1/1992 | Australia . |
| 2036107 | 8/1991 | Canada . |
| 0 052 575 | 5/1982 | European Pat. Off. . |
| 0 091 555 | 10/1983 | European Pat. Off. . |
| 0 131 540 | 1/1985 | European Pat. Off. . |
| 0 202 017 | 11/1986 | European Pat. Off. . |
| 0 224 934 | 6/1987 | European Pat. Off. . |
| 0 324 938 | 7/1989 | European Pat. Off. . |
| 0 327 490 | 8/1989 | European Pat. Off. . |
| 0 381 543 | 8/1990 | European Pat. Off. . |
| 0 458 079 | 11/1991 | European Pat. Off. . |
| 0 458 745 | 11/1991 | European Pat. Off. . |
| 0 494 615 | 7/1992 | European Pat. Off. . |
| 0 554 213 | 8/1993 | European Pat. Off. . |
| 0 606 486 | 7/1994 | European Pat. Off. . |
| 0 611 567 | 8/1994 | European Pat. Off. . |

(List continued on next page.)

OTHER PUBLICATIONS

Raju et al., "Human Serum Albumin Microsperes for Lung Imaging" Isotopenpraxis, 14(2):57–61, 1978.

English Language Abstract of Japanese Patent No. 56–129035 (Document AO6), Patent Abstracts of Japan (JPO and Japio, 1981).

English Language Abstract of Japanese Patent No. 04–145131 (Document AP6), Patent Abstracts of Japan (JPO and Japio, 1992).

Aldrich, J.E. & Johnston, J.R., "Use of the Spinning Disk Technique to Produce Monodisperse Microspheres of Human Serum Albumin for Labelling with Radioisotopes," *Int. J. Appl. Rad. Isot.* 25:15–18 (1974).

(List continued on next page.)

Primary Examiner—John Kight
Assistant Examiner—Michael G. Hartley
Attorney, Agent, or Firm—Sterne, Kessler, Goldstein & Fox P.L.L.C.

[57] ABSTRACT

A process for forming microcapsules comprising (i) providing a solution of a protein in an aqueous solvent and (ii) spraying the said solution into a gas such that the aqueous solvent evaporates, thereby forming hollow microcapsules, characterised in that the aqueous solution contains a liquid of greater volatility than water.

The protein is preferably albumin and the volatile liquid is preferably ethanol.

The microcapsules may be used as ultrasound echogenic contrast agents.

14 Claims, 1 Drawing Sheet

U.S. PATENT DOCUMENTS

| | | | |
|---|---|---|---|
| 5,271,961 | 12/1993 | Mathiowitz et al. | 427/213.31 |
| 5,370,861 | 12/1994 | Klaveness et al. | 424/5 |
| 5,380,519 | 1/1995 | Schneider et al. | 424/9 |
| 5,425,366 | 6/1995 | Reinhardt et al. | 128/662.02 |
| 5,498,421 | 3/1996 | Grinstaff et al. | 424/450 |
| 5,501,863 | 3/1996 | Rössling et al. | 424/489 |
| 5,518,709 | 5/1996 | Sutton et al. | 424/9.52 |
| 5,536,490 | 7/1996 | Klaveness et al. | 424/9.52 |
| 5,543,162 | 8/1996 | Timonen et al. | 426/89 |
| 5,547,656 | 8/1996 | Unger | 424/9.4 |
| 5,567,413 | 10/1996 | Klaveness et al. | 424/9.51 |
| 5,567,414 | 10/1996 | Schneider et al. | 424/9.52 |
| 5,605,673 | 2/1997 | Schutt et al. | 424/9.51 |
| 5,643,553 | 7/1997 | Schneider et al. | 424/9.52 |
| 5,658,551 | 8/1997 | Schneider et al. | 424/9.51 |

FOREIGN PATENT DOCUMENTS

| | | |
|---|---|---|
| 2 660 864 | 10/1991 | France . |
| 56-129035 | 10/1981 | Japan . |
| 4-145131 | 5/1992 | Japan . |
| 4-506931 | 12/1992 | Japan . |
| 6-507884 | 9/1994 | Japan . |
| 227 869 | 11/1992 | New Zealand . |
| 89 0873 | 2/1989 | South Africa . |
| 1 288 583 | 9/1972 | United Kingdom . |
| WO 84/02838 | 8/1984 | WIPO . |
| WO 90/13780 | 11/1990 | WIPO . |
| WO 91/01706 | 2/1991 | WIPO . |
| WO 91/06286 | 5/1991 | WIPO . |
| WO 91/09629 | 7/1991 | WIPO . |
| WO 91/12823 | 9/1991 | WIPO . |
| WO 91/15244 | 10/1991 | WIPO . |
| WO 91/16080 | 10/1991 | WIPO . |
| WO 92/05806 | 4/1992 | WIPO . |
| WO 92/17212 | 10/1992 | WIPO . |
| WO 92/17213 | 10/1992 | WIPO . |
| WO 92/18164 | 10/1992 | WIPO . |
| WO 93/02712 | 2/1993 | WIPO . |
| WO 94/08627 | 4/1994 | WIPO . |
| WO 96/15814 | 5/1996 | WIPO . |
| WO 96/18388 | 6/1996 | WIPO . |

OTHER PUBLICATIONS

Barnhart, J. et al., "Characteristics of Albunex: Air–Filled Albumin Microspheres for Echocardiography Contrast Enhancement," *Invest. Radiol.* 25:s164 (1990).

Basu, S. & Bhattacharya, G., "Some Aspects of the Phenomenon of Coacervation," *Science* 115:544–545 (1952).

Baveja, S. K. et al., "Microencapsulation of soluble pharmaceuticals," *J. Microencapsulation* 3(1):33–37 (1986).

Beller, G. A. et al., "Assessment of Regional Myocardial Perfusion by Positron Emission Tomography after Intracoronary Administration of Gallium–68 Labeled Albumin Microspheres," *J. Computer Assisted Tomography* 3(4):447–452 (1979).

Buchanan, J.W. et al., "Labeling Albumin Microspheres with $^{113m}$In," *J. Nucl. Med.* 10(7):487–490 (1969).

Cheng, K. T. et al., "The Production and Evaluation of Contrast–Carrying Liposomes Made with an Automatic High–Pressure System," *Investigative Radiol.* 22(1):47–55 (1987).

Clausen, G. et al., "Distribution of blood flow in the dog kidney. III. Local uptake of 10 μm and 15 μm microspheres during renal vasodilation and constriction," *Acta Physiol. Scand.* 113: 471–479 (1981).

Conte, U. et al., "Spray Dried Albumin Microspheres Containing Nicardipine," *Eur. J. Pharm. Biopharm.* 40(4):203–208 (Aug. 1994).

Cremers, H. F. M. et al., "Albumin–Heparin Microspheres As Carriers for Cystostatic Agents," *J. Controlled Release* 11:167–179 (1990).

Davis, S. S. and L. Illum, "Microspheres As Drug Carriers," in: *Drug Carrier Systems,* F. H. D. Roerdink and A. M. Kroon, eds., New York: John Wiley & Sons, Ltd., pp. 131–153 (1989).

Deasy, P.B., "Coacervation —Phase Separation Procedures Using Aqueous Vehicles," in: *Microencapsulation and Related Drug Processes,* New York: Marcel Dekker, Inc., pp. 61–69 (1984).

Durand–Keklikian, L. and Partch, R. E., "Microencapsulation of Oil Droplets by Aerosol Techniques –I. Metal Oxide Coatings," *J. Aerosol Sci.* 19(4):511–521 (1988).

Ellison, J.M., "Adaptation of the Spinning Top Generator to Provide Aerosols in the Respirable Range," *Ann. Occup. Hyg.* 10:363–367 (1967).

Feinstein, S.B. et al., "Microbubble Dynamics Visualized in the Intact Capillary Circulation," *JACC* 4(3):595–600 (1984).

Galyean, R.D. & Cotterill, O.J., "Chromatography and Electrophoresis of Native and Spray–Dried Egg White," *J. Food Sci.* 44:1345–1349 (1979).

Grinstaff, M.W. & Suslick, K.S., "Air–filled proteinaceous microbubbles: Synthesis of an echo–contrast agent," *Proc. Natl. Acad. Sci. USA* 88:7708–7710 (1991).

Gupta, P.K. & Hung, C.T., "Albumin microspheres I: physico–chemical characteristics," *J. Microencapsulation* 6(4):427–462 (1989).

Haghpanah, M. et al., "Drug delivery to the lung using albumin microparticles," 131st British Pharmaceutical Conference, London, England, *J. Pharm. Pharmacol.* 46(Suppl. 2):1138 (Sep. 1994).

Heller, J., "Controlled release of biologically active compounds from bioerodible polymers," *Biomaterials* 1:51–57 (1980).

Kawashima, Y. et al., "Preparation of multiple unit hollow microspheres (microballons) with acrylic resin containing tranilast and their drug release characteristics (in vitro) and floating behavior (in vivo)," *J. Controlled Release* 16:279–290 (1991).

Kondo, A., in: *Microcapsule Processing and Technology,* Van Valkenburg, J.W. (ed.), New York: Marcel Dekker, Inc., pp. 18–20, 61, 68, 70, 90–92, 106–109, 118–119 (1980).

Kramer, P.A., "Albumin Microspheres as Vehicles for Achieving Specificity in Drug Delivery," *J. Pharm. Sci.* 63(10):1646–1647 (1974).

Kwok, K. K. et al., "Production of 5–15 μm Diameter Alginate–Polylysine Microcapsules by an Air–Atomization Technique," *Pharm. Res.* 8(3):341–344 (1991).

Levy, M.–C. and Andry, M.–C., "Mixed–walled microcapsules made of cross–linked proteins and polysaccharides: preparation and properties," *J. Microencapsulation* 8(3):335–347 (1991).

McArdle, C. S. et al., "Cytotoxic–loaded albumin microspheres: a novel approach to regional chemotherapy," *Br. J. Surg.* 75:132–134 (1988).

Modler, H.W. & Emmons, D.B., "Calcium as an Adjuvant for Spray–Drying Acid Whey," *J. Dairy Sci.* 61:294–299 (1978).

Morris, N.J. & Warburton, B., "Three-ply walled w/o/w microcapsules formed by a multiple emulsion technique," *J. Pharm. Pharmacol.* 34:475–479 (1982).

Morris, N.J. & Warburton, B., "Particle size analysis of microcapsules," *J. Pharm. Pharmacol.* 36:73–76 (1984).

Omotosho, J.A. et al., "The nature of the oil phase and the release of solutes from multiple (w/o/w) emulsions," *J. Pharm. Pharmacol.* 38:865–870 (1986).

Ophir, J. et al., "Aqueous Solutions as Potential Ultrasonic Contrast Agents," *Ultrasonic Imaging* 1(3):265–279 (1979).

Ophir, J. et al., "Ultrasonic Backscatter from Contrast Producing Collagen Microspheres," *Ultrasonic Imaging* 2:67–77 (1980).

Pande, S. et al., "Preparation, characterization and performance evaluation of neomycin–HSA microspheres," *J. Microencapsulation* 7(2):155–165 (1990).

Parkinson, T.L., "Effects of Spray–drying and Freezing on the Proteins of Liquid Whole Egg," *J. Sci. Fd Agric.* 26:1625–1637 (1975).

Porter, C. J. H., "The polyoxyethylene/polyoxpropylene block co–polymer Poloxamer–407 selectively redirects intravenously injected microspheres to sinusoidal endothelial cells of rabbit bone marrow," *FEBS Lett.* 305(1):62–66 (1992).

Pryzborowski, M. et al., "Preparation of HSA Microspheres in a One–Step Thermal Denaturation of Protein Aerosol Carried in Gas–Medium," *Eur. J. Nucl. Med.* 7:71–72 (1982).

Raju, A. et al., "Human Serum Albumin Microspheres for Lung Imaging —Preparation and Evaluation," *Isotopenpraxis* 14:57–61 (1978).

Rettenmaier, M.A. et al., "In Vivo Alteration of RES Phagocytosis by Magnetic Albumin Microspheres," *J. Clin. Lab. Immunol.* 17:99–103 (1985).

Rosenberg, M. et al., "Factors Affecting Retention in Spray–Drying Microencapsulation of Volatile Materials," *J. Agric. Food Chem.* 38:1288–1294 (1990).

Sato, T. et al., "Porous Biodegradable Microspheres for Controlled Drug Delivery. I. Assessment of Processing Conditions and Solvent Removal Techniques," *Pharm. Res.* 5(1):21–30 (1988).

Scheffel, U. et al., "Albumin Microspheres for Study of the Reticuloendothelial System," *J. Nucl. Med.* 13:498–503 (1972).

Schlief, R., "Ultrasound contrast agents," *Curr. Opin. Radiol.* 3:198–207 (1991).

Schneider, M. et al., "Polymeric Microballoons as Ultrasound Contrast Agents: Physical and Ultrasonic Properties Compared with Sonicated Albumin," *Invest. Radiol.* 27(2):134–139 (1992).

Schroeder, H.G. et al., "Distribution of Radiolabeled Subvisible Microspheres after Intravenous Administration to Beagle Dogs," *J. Pharm. Sci.* 67(4):504–507 (1978).

Shah, M.V. et al., "An evaluation of albumin microcapsules prepared using a multiple emulsion technique," *J. Microencapsulation* 4(3):223–238. (1987).

Shapiro, J.R. et al., "Intravenous Contrast Echocardiography With Use of Sonicated Albumin in Humans: Systolic Disappearance of Left Ventricular Contrast After Transpulmonary Transmission," *JACC* 16(7):1603–1607 (1990).

Takenaka, H. et al., "Preparation of Enteric–Coated Microcapsules for Tableting by Spray–Drying Technique and In Vitro Simulation of Drug Release from the Tablet in GI Tract," *J. Pharm. Sci.* 69(1):1388–1392 (1980).

Takenaka, H. et al., "Mechanical Properties, Dissolution Behavior and Stability to Oxidation of L–Ascorbyl–monostearate Microcapsules prepared by a Spray–Drying Polycondensation Technique," *Chem. Pharm. Bull.* 30(6):2189–2195 (1982).

Violante, M. R. et al., "Biodistribution of Particulate Hepatolienographic CT Contrast Agent: A Study of Iodopamide Ethyl Ester in the Rat," *Investigative Radiol.* 16(1):40–45 (1981).

Wheatley, M.A. et al., "Contrast agents for diagnostic ultrasound: development and evaluation of polymer–coated microbubbles," *Biomaterials* 11:713–717 (1990).

White, C. et al., "Biodistribution and Clearance of Contrast–Carrying MREV Liposomes," *Investigative Radiol.* 25(10):1125–1129 (1990).

Widder, K.J. et al., "Magnetically Responsive Microspheres and Other Carriers for the Biophysical Targeting of Antitumor Agents," *Adv. Pharmacol. Chemother.* 16:213–271 (1979).

Wilkins, D. J. and Myers, P. A., "Studies on the Relationship Between the Electrophoretic Properties of Colloids and Their Blood Clearance and Organ Distribution in the Rat," pp. 568–576 1966.

Zhang, D. et al., "Histochemical studies on the mechanism of macromolecule leakage across the glomerular capillary wall," *Histochem.* 96:115–121 (1991).

PREPARATION OF HOLLOW MICROCAPSULES BY SPRAY-DRYING AN AQUEOUS SOLUTION OF A WALL-FORMING MATERIAL AND A WATER-MISCIBLE SOLVENT

The present invention relates to the preparation of hollow proteinaceous microcapsules. One use for these microcapsules is to enhance ultrasound imaging.

The fact that air bubbles in the body can be used for echocardiography has been known for some time.

WO 92/18164 discloses the spray-drying of a solution of a wall-forming material, preferably a protein such as albumin, to form microcapsules. In WO 94/08627, the pressure at which the solution is sprayed into the heated chamber is reduced, to form larger microcapsules, or the half-life of the microcapsules in the bloodstream is increased, for example by including a surfactant in the solution which is sprayed, or the microcapsules are targeted to a selected part of the body, for example by suspending them in a solution of an electrically charged compound.

U.S. Pat. No. 4,420,442 (Sands; PQ Corpn) discloses adding organic solvents to dispersions of film-forming solids, before the suspensions are spray-dried to form hollow microspheres, but the solvents (for example cellosolve or diglyme) were less volatile than water.

We have now found that, by including a volatile compound in the aqueous solution which is spray-dried, microcapsules with improved properties can be formed, in higher yield, with narrower size distribution and thinner shells.

One aspect of the invention provides a process for forming microcapsules comprising (i) providing a solution of an aqueously-soluble material in an aqueous solvent and (ii) spraying the said solution into a gas such that the aqueous solvent evaporates, thereby forming hollow microcapsules, characterised in that the aqueous solution contains a liquid of greater volatility than water.

Figure 1:
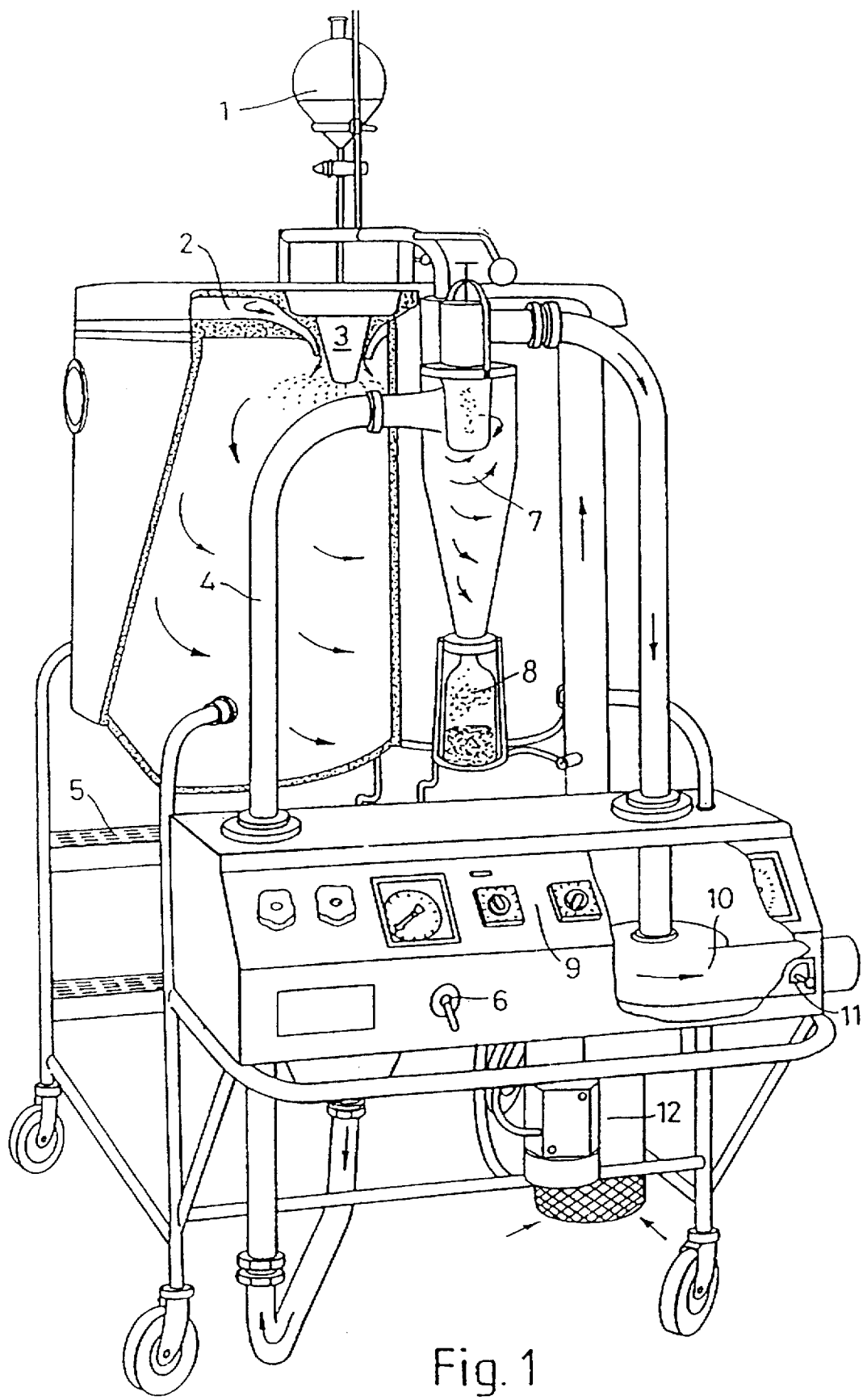
FIG. 1 is a partly cut away perspective view from the front and one side of a suitable spray-drying apparatus.

Suitable volatile liquids include ethanol (the preferred volatile liquid) (boiling point 78.3° C.), methanol (b.p. 64.5° C.), and acetone (b.p. 56° C.). The volatile liquid needs to act as a solvent for the wall-forming material and be miscible with water at the ratios used.

The proportion of the aqueous solution which is the volatile liquid will vary according to the identity of the volatile compound, the concentration and identity of the wall-forming material, the temperature and pressures at which the solution is to be sprayed, and the microcapsule product desired. Typically, between 0.1% and 80% v/v, preferably 1–50% v/v and most preferably 5–30% v/v, for example about 20% v/v, of the solution is the volatile liquid. Mixtures of volatile liquids may be used, in which case these percentages refer to the total content of volatile liquid.

The spray-drying may be a one step process such as to provide the desired microcapsule product immediately. Alternatively, the immediate product may be subjected to further process steps, for example heating to further cross-link and insolubilise the protein shell of the microcapsules. This constitutes a two step process.

For a product which is to be injected into the human bloodstream, for example as an echogenic contrast agent in ultrasound diagnostic procedures (which is one intended use of the product), the total process is preferably carried out under sterile conditions. Thus, the protein solution is sterile and nonpyrogenic, the gas in the chamber is first passed through a 0.2 μm filter, the spray-drier is initially autoclaved and so on. Alternatively, or as well, the final product may be sterilised, for example by exposure to ionising radiation.

The wall-forming material is a water-soluble material, preferably a protein (the term being used to include non-naturally occurring polypeptides and polyamino acids). For example, it may be collagen, gelatin or (serum) albumin, in each case (if the microcapsules are to be administered to humans) preferably of human origin (ie derived from humans or corresponding in structure to the human protein) or polylysine or polyglutamate. It may be human serum albumin (HA) derived from blood donations or from the fermentation of microorganisms (including cell lines) which have been transformed or transfected to express HA. Alternatively, simple or complex carbohydrates, simple amino acids or fatty acids can be used, for example lysine, mannitol, dextran, palmitic acid or behenic acid.

Techniques for expressing HA (which term includes analogues and fragments of human albumin, for example those of EP-A-322094, and polymers of monomeric albumin) are disclosed in, for example, EP-A-201239 and EP-A-286424. All references are included herein by reference. "Analogues and fragments" of HA include all polypeptides (i) which are capable of forming a microcapsule in the process of the invention and (ii) of which a continuous region of at least 50% (preferably at least 75%, 80%, 90% or 95%) of the amino acid sequence is at least 80% homologous (preferably at least 90%, 95% or 99% homologous) with a continuous region of at least 50% (preferably 75%, 80%, 90% or 95%) of a nature-identical human albumin. HA which is produced by recombinant DNA techniques may be used. Thus, the HA may be produced by expressing an HA-encoding nucleotide sequence in yeast or in another microorganism and purifying the product, as is known in the art. Such material lacks the fatty acids associated with serum-derived material. Preferably, the HA is substantially free of fatty acids; ie it contains less than 1% of the fatty acid level of serum-derived material. Preferably, fatty acid is undetectable in the HA.

The aqueous solution or dispersion is preferably 0.1 to 50% w/v, more preferably about 1.0–25.0% w/v or 5.0–30.0% w/v protein, particularly when the material is albumin. About 5–15% w/v is optimal. Mixtures of wall-forming materials may be used, in which case the percentages in the last two sentences refer to the total content of wall-forming material.

The preparation to be sprayed may contain substances other than the wall-forming material, water and volatile liquid. Thus, the aqueous phase may contain 1–20% by weight of water-soluble hydrophilic compounds like sugars and polymers as stabilizers, eg polyvinyl alcohol (PVA), polyvinyl pyrrolidone (PVP), polyethylene glycol (PEG), gelatin, polyglutamic acid and polysaccharides such as starch, dextran, agar, xanthan and the like.

Functional agents may be included, for example at 1.0–40.0% w/w, such as X-ray contrast agents (for example Hexabrix (ioxaglic acid), Optiray (ioversol), Omnipaque (iohexol) or Isovice (iopamidol)) or magnetic resonance imaging agents (for example colloidal iron oxide or gadolinium chelates, eg gadopentetic acid).

Similar aqueous phases can be used as the carrier liquid in which the final microcapsule product is suspended before use. Surfactants may be used (0.1–5% by weight) including most physiologically acceptable surfactants, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Other surfactants include free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and triglycerides of saturated or unsaturated fatty acids, glycerides or soya-oil and sucrose. Preferably, however, the carrier liquid does not contain a surfactant.

Additives can be incorporated into the wall of the microcapsules to modify the physical properties such as dispersibility, elasticity and water permeability.

Among the useful additives, one may cite compounds which can "hydrophobize" the wall in order to decrease water permeability, such as fats, waxes and high molecular-weight hydrocarbons. Additives which increase dispersibility of the microcapsules in the injectable liquid-carrier are amphipathic compounds like the phospholipids; they also increase water permeability and rate of biodegradability. Preferably, however, the microcapsules do not contain additives which increase the dispersibility of the microcapsules, as we have found that they are unnecessary, at least when the microcapsules are made of albumin.

The quantity of additives to be incorporated in the wall is extremely variable and depends on the needs. In some cases no additive is used at all; in other cases amounts of additives which may reach about 40.0% by weight of the wall are possible.

The solution of the wall-forming material is atomized and spray-dried by any suitable technique which results in discrete microcapsules of 0.05–50.0 μm diameter. These figures refer to at least 90% of the volume of microcapsules, the diameter being measured with a Coulter Multisizer II. The term "microcapsules" means hollow particles enclosing a space, which space is filled with a gas or vapour but not with any solid materials. Honeycombed particles resembling the confectionery sold in the UK as "Maltesers" (™) are not formed. It is not necessary for the space to be totally enclosed (although this is preferred) and it is not necessary for the microcapsules to be precisely spherical, although they are generally spherical. If the microcapsules are not spherical, then the diameters referred to above relate to the diameter of a corresponding spherical microcapsule having the same mass and enclosing the same volume of hollow space as the non-spherical microcapsule.

The atomizing comprises forming an aerosol of the preparation by, for example, forcing the preparation through at least one orifice under pressure into, or by using a centrifugal atomizer in a chamber of warm air or other inert gas. The chamber should be big enough for the largest ejected drops not to strike the walls before drying. If the microcapsules are intended to be injected into the bloodstream for diagnostic imaging, then the gas or vapour in the chamber is clean (ie preferably sterile and pyrogen-free) and, non-toxic when administered into the bloodstream in the amounts concomitant with administration of the microcapsules in echocardiography. The rate of evaporation of the liquid from the protein preparation should be sufficiently high to form hollow microcapsules but not so high as to burst the microcapsules. The rate of evaporation may be controlled by varying the gas flow rate, concentration of protein in the protein preparation, nature of liquid carrier, feed rate of the solution and, most importantly, the temperature of the gas encountered by the aerosol. Small size distributions are achieved by spray-drying in which there is a combination of low feed stock flow rate with very high levels of atomization and drying air. The effect is to produce microcapsules of very defined size and tight size distribution. Several workers have designed equations to define the mean droplet size of pneumatic nozzles; a simple version of the various parameters which affect mean droplet size is as follows:

$$D = A/(V^2.d)^a + B.(M_{air}/M_{liq})^{-b}$$

where
D=Mean droplet size
A=Constant related to nozzle design
B=Constant related to liquid viscosity
V=Relative air velocity between liquid and nozzle
d=Air density
$M_{air}$ and $M_{liq}$=Mass of air and liquid flow
a and b=Constants related to nozzle design
(For the avoidance of doubt, V is squared, $(V^2.d)$ is raised to the power of a and $(M_{air}/M_{liq})$ is raised to the power of minus b.)

Clearly, for any given nozzle design, the droplet size is most affected by the relative velocity at the nozzle and concurrently the mass ratio of air to liquid. For most-common drying uses, the air to liquid ratio is in the range of 0.1–10 and at these ratios it appears that the average droplet size is 15–20 μm. For the production of microcapsules in the size range described herein we generally use air to liquid ratios ranging from 20–1600. The effect is to produce particles at the high ratios which are exceedingly small by comparative standards, with very narrow size distributions. For microcapsules produced at the lower ratios of air to liquid, slightly larger particles are produced, but they still nevertheless have right size distributions which are superior to microcapsules produced by emulsion techniques.

With an albumin concentration of 5.0–25.0% in water, an inlet gas temperature of at least about 100° C., preferably at least 110° C., is generally sufficient to ensure hollowness and the temperature may be as high as 250° C. without the capsules bursting. About 180°–240° C., preferably about 210°–230° C. and most preferably about 220° C., is optimal, at least for albumin. The temperature may, in the one step version of the process of the invention, be sufficient to insolubilise at least part (usually the outside) of the wall-forming material and frequently substantially all of the wall-forming material. Since the temperature of the gas encountered by the aerosol will depend also on the rate at which the aerosol is delivered and on the liquid content of the protein preparation, the outlet temperature may be monitored to ensure an adequate temperature in the chamber. An outlet temperature of 40°–150° C. has been found to be suitable.

In the two step process, if the wall-forming material is a protein, the intermediate microcapsules comprise typically 96–98% monomeric protein and retain the same water solubility as the wall-forming material itself. They have a limited in vivo life time for ultrasound imaging. They may, however, be used for ultrasound imaging, or they may be stored and transported before the second step of the two step process is carried out. They therefore form a further aspect of the invention.

In the second step of the process, the intermediate microcapsules prepared in the first step are fixed and rendered less water-soluble so that they persist for longer whilst not being so insoluble and inert that they are not biodegradable. This step also strengthens the microcapsules so that they are better able to withstand the rigours of administration, vascular shear and ventricular pressure. If the microcapsules burst, they become less echogenic. Schneider et al (1992) *Invest. Radiol.* 27, 134–139 showed that prior art sonicated albumin microbubbles do not have this strength and rapidly lose their echogenicity when subjected to pressures typical of the left ventricle. The second step of the process may employ heat (for example microwave heat, radiant heat or hot air, for example in a conventional oven), ionising irradiation (with, for example, a 10.0–100.0 kGy dose of gamma rays) or chemical cross-linking in solvents using, for example, formaldehyde, glutaraldehyde, ethylene oxide or other agents for cross-linking proteins and is carried out on the substantially dry intermediate microcapsules formed in the first step, or on a suspension of such microcapsules in a liquid in which the microcapsules are insoluble, for example a suitable solvent. In the one step version of the process, a cross-linking agent such as glutaraldehyde may be sprayed into the spray-drying chamber or may be introduced into the protein preparation just upstream of the spraying means. Alternatively, the temperature in the chamber may be high enough to insolubilise the microcapsules.

The final product, measured in the same way as the intermediate microcapsules, may, if one wishes, consist of microcapsules having a diameter of 0.1 to 50.0 µm, but volume ranges of 0.1 to 20.0 µm and especially 1.0 to 8.0 µm are obtainable with the process of the invention and are preferred for echocardiography. One needs to take into account the fact that the second step may alter the size of the microcapsules in determining the size produced in the first step.

It has been found that the process of the invention can be controlled in order to obtain microcapsules with desired characteristics. Thus, the pressure at which the protein solution is supplied to the spray nozzle may be varied, for example from $1.0–20.0 \times 10^5$ Pa, preferably $5.0–10.0 \times 10^5$ Pa and most preferably about $7.5 \times 10^5$ Pa. Similarly, the flow rate of the liquid may be varied. Other parameters may be varied as disclosed above and below. In this way, novel microcapsules may be obtained. We have found that microcapsules formed from feedstocks containing volatile components provide more intact hollow capsules, with smoother surfaces, and are smaller than capsules formed in the absence of a volatile component.

In particular, a product having a high degree of reflectivity, relative to the amount of wall-forming material, may be obtained. For example, a homogeneous suspension of 13 µg/ml of microcapsules can provide a reflectivity to 3.5 MHz ultrasound of at least −1.0 dB. Higher reflectivities than −0.3 may be unnecessary, and a reflectivity of around −0.7 to −0.5 is convenient.

Preferably, at least 50% of the protein in the walls of the microcapsules is cross-linked. Preferably, at least 75%, 90%, 95%, 98.0%, 98.5% or 99% of the protein is sufficiently cross-linked to be resistant to extraction with a 1% HCl solution for 2 minutes. Extracted protein is detected using the Coomassie Blue protein assay, Bradford. The degree of cross-linking is controlled by varying the heating, irradiation or chemical treatment of the protein. During the cross-linking process, protein monomer is cross-linked and quickly becomes unavailable in a simple dissolution process, as detected by gel permeation HPLC or gel electrophoresis, as is shown in Example 3 below. Continued treatment leads to further cross-linking of already cross-linked material such that it becomes unavailable in the HCl extraction described above. During heating at 175° C., HA microcapsules in accordance with the invention lose about 99% of HCl-extractable protein over the course of 20 minutes, whereas, at 150° C., 20 minutes' heating removes only about 5% HCl-extractable protein, 30 mins removes 47.5%, 40 mins 83%, 60 mins 93%, 80 mins 97% and 100 mins removes 97.8% of the HCl-extractable protein. To achieve good levels of cross-linking therefore, the microcapsules may be heated at 175° C. for at least 17–20 mins, at 150° C. for at least 80 mins and at other temperatures for correspondingly longer or shorter times.

The microcapsules of the present invention can be stored dry in the presence or in the absence of additives to improve conservation, prevent coalescence or aid resuspension. As additives, one may select from 0.1 to 200.0% by weight of water-soluble physiologically acceptable compounds such as mannitol, galactose, lactose or sucrose or hydrophilic polymers like dextran, xanthan, agar, starch, PVP, polyglutamic acid, polyvinylalcohol (PVA) and gelatin. The useful life-time of the microcapsules in the injectable liquid carrier phase, ie the period during which useful echographic signals are observed, can be controlled to last from a few minutes to several months depending on the needs; this can be done by controlling the porosity, solubility or degree of cross-linking of the wall. These parameters can be controlled by properly selecting the wall-forming materials and additives and by adjusting the evaporation rate and temperature in the spray-drying chamber.

In order to minimise any agglomeration of the microcapsules, the microcapsules can be milled with a suitable inert excipient using a Fritsch centrifugal pin mill equipped with a 0.5 mm screen, or a Glen Creston air impact jet mill. Suitable excipients are finely milled powders which are inert and suitable for intravenous use, such as lactose, glucose, mannitol, sorbitol, galactose, maltose or sodium chloride. Once milled, the microcapsules/excipient mixture can be suspended in aqueous medium to facilitate removal of non-functional/defective microcapsules, or it can be placed in final containers for distribution without further processing. To facilitate subsequent reconstitution in the aqueous phase, a trace amount of surfactant can be included in the milling stage and/or in the aqueous medium to prevent agglomeration. Anionic, cationic and non-ionic surfactants suitable for this purpose include poloxamers, sorbitan esters, polysorbates and lecithin.

The microcapsule suspension may then be allowed to float, or may be centrifuged to sediment any defective particles which have surface defects which would, in use, cause them to fill with liquid and be no longer echogenic.

The microcapsule suspension may then be remixed to ensure even particle distribution, washed and reconstituted in a buffer suitable for intravenous injection such as isotonic mannitol. The suspension may be aliquoted for freeze drying and subsequent sterilisation by, for example, gamma irradiation, dry heating or ethylene oxide.

An alternative method for deagglomeration of the insolubilised or fixed microcapsules is to suspend them directly in an aqueous medium containing a suitable surfactant, for example poloxamers, sorbitan esters, polysorbates and lecithin. Deagglomeration may then be achieved using a suitable homogeniser.

The microcapsule suspension may then be allowed to float or may be centrifuged to sediment the defective particles, as above, and further treated as above.

In a preferred embodiment of the invention, the product of the heat fixing step is de-agglomerated by milling as above.

Although the microcapsules of this invention can be marketed in the dry state, more particularly when they are designed with a limited, life time after injection, it may be desirable to also sell ready-made preparations, ie suspensions of microcapsules in an aqueous liquid carrier ready for injection.

The product is generally, however, supplied and stored as a dry powder and is suspended in a suitable sterile, non-pyrogenic liquid just before administration. The suspension is generally administered by injection of about 1.0–10.0 ml into a suitable vein such as the cubital vein or other bloodvessel. A microcapsule concentration of about $1.0 \times 10^5$ to $1.0 \times 10^{12}$ particles/ml is suitable, preferably about $5.0 \times 10^5$ to $5.0 \times 10^9$.

Although ultrasonic imaging is applicable to various animal and human body organ systems, one of its main applications is in obtaining images of myocardial tissue and perfusion or blood flow patterns.

The techniques use ultrasonic scanning equipment consisting of a scanner and imaging apparatus. The equipment produces visual images of a predetermined area, in this case the heart region of a human body. Typically, the transducer is placed directly on the skin over the area to be imaged. The scanner houses various electronic components including ultrasonic transducers. The transducer produces ultrasonic waves which perform a sector scan of the heart region. The ultrasonic waves are reflected by the various portions of the heart region and are received by the receiving transducer and processed in accordance with pulse-echo methods known in the art. After processing, signals are sent to the imaging apparatus (also well known in the art) for viewing.

In the method of the present invention, after the patient is "prepped" and the scanner is in place, the microcapsule suspension is injected, for example through an arm vein. The contrast agent flows through the vein to the right venous side of the heart, through the main pulmonary artery leading to the lungs, across the lungs, through the capillaries, into the pulmonary vein and finally into the left atrium and the left ventricular cavity of the heart.

With the microcapsules of this invention, observations and diagnoses can be made with respect to the amount of time required for the blood to pass through the lungs, blood flow patterns, the size of the left atrium, the competence of the mitral valve (which separates the left atrium and left ventricle), chamber dimensions in the left ventricular cavity and wall motion abnormalities. Upon ejection of the contrast agent from the left ventricle, the competence of the aortic valve also may be analyzed, as well as the ejection fraction or percentage of volume ejected from the left ventricle. Finally, the contrast patterns in the tissue will indicate which areas, if any, are not being adequately perfused.

In summary, such a pattern of images will help diagnose unusual blood flow characteristics within the heart, valvular competence, chamber sizes and wall motion, and will provide a potential indicator of myocardial perfusion.

The microcapsules may permit left heart imaging from intravenous injections. The albumin microcapsules, when injected into a peripheral vein, may be capable of transpulmonary passage. This results in echocardiographic opacification of the left ventricle (LV) cavity as well as myocardial tissue.

Besides the scanner briefly described above, there exist other ultrasonic scanners, examples of which are disclosed in U.S. Pat. Nos. 4,134,554 and 4,315,435. Basically, these patents relate to various techniques including dynamic cross-sectional echography (DCE) for producing sequential two-dimensional images of cross-sectional slices of animal or human anatomy by means of ultrasound energy at a frame rate sufficient to enable dynamic visualisation of moving organs. Types of apparatus utilised in DCE are generally called DCE scanners and transmit and receive short, sonic pulses in the form of narrow beams or lines. The reflected signals' strength is a function of time, which is converted to a position using a nominal sound speed, and is displayed on a cathode ray tube or other suitable devices in a manner somewhat analogous to radar or sonar displays. While DCE can be used to produce images of many organ systems including the liver, gall bladder, pancreas and kidney, it is frequently used for visualisation of tissue and major blood vessels of the heart.

The microcapsules may be used for imaging a wide variety of areas, even when injected at a peripheral venous site. Those areas include (without limitation): (1) the venous drainage system to the heart; (2) the myocardial tissue and perfusion characteristics during an exercise treadmill test or the like; and (3) myocardial tissue after an oral ingestion or intravenous injection of drugs designed to increase blood flow to the tissue. Additionally, the microcapsules may be useful in delineating changes in the myocardial tissue perfusion due to interventions such as (1) coronary artery vein grafting; (2) coronary artery angioplasty (balloon dilation of a narrowed artery); (3) use of thrombolytic agents (such as streptokinase) to dissolve clots in coronary arteries; or (4) perfusion defects or changes due to a recent heart attack.

Furthermore, at the time of a coronary angiogram (or a digital subtraction angiogram) an injection of the microcapsules may provide data with respect to tissue perfusion characteristics that would augment and complement the data obtained from the angiogram procedure, which identifies only the anatomy of the blood vessels.

Through the use of the microcapsules of the present invention, other noncardiac organ systems including the liver, spleen and kidney that are presently imaged by ultrasonic techniques may be suitable for enhancement of such currently obtainable images, and/or the generation of new images showing perfusion and flow characteristics that had not previously been susceptible to imaging using prior art ultrasonic imaging techniques.

Preferred aspects of the present invention will now be described by way of example and with reference to FIG. 1, which is a partly cut away perspective view from the front and one side of suitable spray-drying apparatus for the first stage of the process of the invention.

EXAMPLE 1

Spray-drying equipment

A suitable spray dryer (FIG. 1) is available from A/S Niro Atomizer, Soeborg, Denmark under the trade designation "Mobile Minor". The spray dryer comprises a reservoir 1 for the protein solution and a ceiling air disperser 2 which ensures effective control of the air flow pattern. Swirling air is directed around the rotary atomizer or nozzle atomiser 3 (for example type M-02/B Minor), driven by an air turbine at an air pressure of rain 4.0 bar and up to max 6.0 bar. At 6.0 bar an atomizer wheel speed of approx 33,000 rpm is reached. Turning on and off the compressed air to the atomizer is done by means of a valve placed in the instrument panel 9. The maximum consumption of compressed air to the atomizer is 17 $Nm^3$/h at a pressure of 6.0 bar. All parts coming into contact with the liquid feed and powder are made of stainless steel AISI 316, except for the pump feed tube and the atomizer wheel, which is made of stainless steel AISI 329, made to resist high centrifugal force.

The machine, has steps 5 for access to the chamber top and a switch 6 for an air valve for activation of a pneumatic lifting device when raising the chamber lid.

The drying chamber has an inside made of stainless steel AISI 316, well insulated with Rockwool (™), and covered outside with a mild steel sheeting. The roof of the drying chamber is made inside of stainless steel AISI 316 and outside of stainless steel AISI 304.

An air disperser 2 made of stainless steel AISI 304 is used for distribution of the air in the drying chamber in order to achieve the best possible drying effect. An air duct 4, made of stainless steel AISI 316, provides lateral transportation of the exhaust air and the powder to the cyclone 7, which is made of stainless steel AISI 316 and designed to separate the powder and air.

A closing valve of the butterfly valve type, also made of stainless steel AISI 316 and having a gasket of silicone rubber, is used for powder discharge under the cyclone into a powder collecting glass jar 8 tightly placed under the cyclone by means of a spring device.

A centrifugal exhaust fan 10 made of silumin, with 3-phase squirrel-cage motor, 0.25 kW, and V-belt drive with belt-guard, draws air and powder through the drying chamber and cyclone. A damper 11 controls the air flow.

An air heater 12 heats the drying air by means of electricity (total consumption 7.5 kWh/h, infinitely variable) and can give inlet air temperatures of up to about 350° C., although this is generally too high for preparing the microcapsules of the invention.

Evaporative capacity

| Drying Air | Inlet Air Temperature | Outlet Air Temperature | Evaporative Capacity |
| --- | --- | --- | --- |
| 85 kg/h | 150° C. | 80° C. | 1,3 kg/h |
| 85 kg/h | 170° C. | 85° C. | 1,7 kg/h |
| 80 kg/h | 200° C. | 90° C. | 2,5 kg/h |
| 80 kg/h | 240° C. | 90° C. | 3,4 kg/h |
| 75 kg/h | 350° C. | 90° C. | 7,0 kg/h |

Equipment for two-fluid nozzle atomization may be added, which is made of stainless steel AISI 316, consisting of entrance pipe with nozzle holder and nozzle, to be placed in the ceiling of the drying chamber. The equipment includes an oil/water separator, reduction valve and pressure gauge for compressed air to the two-fluid nozzle. Consumption of compressed air: 8–15 kg/h at a pressure of 0.5–2.0 bar (0.5–2.0×$10^5$ Pa).

A suitable feed pump for transport of wall-forming preparation feed to the atomizer device is a peristaltic pump. The pump is provided with a motor (1×220V, 50 Hz, 0.18 kW) and a continuously variable gear for manual adjustment. A feed pipe made of silicone hose leads from a feed tank (local supply) through the feed pump to the atomization device.

An absolute air filter, consisting of prefilter, filter body in stainless steel and absolute air filter, is used for the treatment of the ingoing drying air to render it completely clean.
Process A 10.0% w/v solution of sterile, pyrogen-free rHA in pyrogen-free water (suitable for injection) with 25.0% v/v ethanol was pumped to the nozzle of a two fluid nozzle atomizer mounted in the commercial spray drying unit described above. The peristaltic pump speed was maintained at a rate of approximately 4.0 g/minute such that with an inlet air temperature of 220° C. the outlet air temperature was maintained at 95° C.

Compressed air was supplied to the two fluid atomizing nozzle at 2.0–10.0 Bar (2.0–6.0×$10^5$ Pa). In this range microcapsules with a mean size of 2.0–3.0 μm are obtained.

Typically an increase in mean particle size (by reduced atomization pressure) led to an increase in the amount of microcapsules over 10 μm in size (see Table 1).

TABLE 1

EFFECTS OF ATOMIZATION PRESSURE ON FREQUENCY OF MICROCAPSULES OVER 10 μM IN DIAMETER

| Atomization Pressure (× $10^5$ Pa) | % Frequency over 10 μm |
| --- | --- |
| 6.0 | 0.8 |
| 5.0 | 3.0 |
| 3.5 | 6.6 |
| 2.5 | 8.6 |
| 2.0 | 13.1 |

A pressure of 5.0×$10^5$ Pa was used to generate the microcapsules in this specific example.

In the second step of the process, 5 g of microcapsules were heated in a glass beaker using a Gallenkamp fan oven. A temperature of 175° C. for 1 hour was sufficient to yield microcapsules with 100% fixation as determined by HPLC. The effect of this heat fixation was to increase the in vitro echogenic half life from a few seconds to in excess of 30 minutes. By altering the temperature and length of incubation it is possible to vary the degree of fixation between about 5% and 100%.

Following heat fixation, the microcapsules were deagglomerated and dispersed into water in one of two ways. Method 1 involved first mixing the heat fixed spheres with an equal weight of finely milled lactose (mean diameter 5 μm).

The mixture was then passed through a Fritsch centrifugal mill with a 0.5 mm screen and 12 tooth rotor. The milled spheres were collected and passed through the mill a second time to ensure complete mixing had occurred. The milled powder was then resuspended in water containing 1 mg.ml$^{-1}$ Pluronic F68 (™). Typically 10 g of microcapsules and lactose was added to 100 ml of water and Pluronic F68. Method 2 for deagglomeration involves adding 5 g of the heat-fixed microcapsules to 100 ml of water containing 100 mg of Pluronic F68. The microcapsules were dispersed using a Silverson homogeniser (model L4R with a 2.54 cm tubular homogenising probe and a high shear screen) and homogenising for 60 seconds.

The resuspended spheres were separated into intact (gas containing) and broken spheres using a flotation technique. The gas-containing spheres were seen to float to the surface over a 1 hour period and were decanted from the sinking fraction which does not contain the gas required.

The separation process can be accelerated by centrifugation. A 30 second centrifugation at 5000×g is sufficient to separate the two fractions.

Following separation the intact microcapsules were freeze-dried in the presence of lactose and Pluronic F68. Optimal conditions for freeze drying involved resuspending 30 mg of microcapsules in 5 ml of water containing 50 mg of lactose and 5 mg of Pluronic F68. The freeze-dried microcapsules can be redispersed in a liquid (eg water, saline) to give a monodisperse distribution.

EXAMPLE 2

Microcapsules were prepared as in Example 1 but under the conditions detailed below.

A 100±10 mg/ml solution of sterile, pyrogen-free serum-derived human albumin in pyrogen-free water (suitable for injection) with 25% w/w ethanol was used as the spray drying feedstock.

Using a peristaltic pump, the albumin feedstock was pumped at a rate of 4±1.5 g/min such that, with an inlet temperature of 220°±0.5° C., an outlet temperature of 80°±10° C. was maintained.

Additional spray-drying conditions were as follows: air flow, 50±2%; atomization pressure, 8.0±0.5 barg; drying air flow, 9±2 mm $H_2O$.

The microcapsules produced were heat-fixed at a temperature of 176°±2° C. for 55±5 min in 5±1 g aliquots in 250 ml stainless steel beakers.

Following heat-fixation, the microcapsules were deagglomerated. Glucose was added to the pooled microcapsules at a ratio of 2:1, mixed and milled with a Glen Creston air impact jet mill.

The deagglomerated microcapsules were filled into glass vials, and the vials purged with nitrogen, sealed and capped. The product was terminally sterilised by irradiating at a dose of between 25–35 kGy.

EXAMPLE 3

ASSAY OF FREE MONOMERIC ALBUMIN IN MICROCAPSULES

A 1 ml volume of ethanol was added to 100 mg of microcapsules in a 20 ml glass bottle and sonicated for 30 seconds. To this suspension 19 ml of $H_2O$ were added.

The mixture was centrifuged in a bench-top microfuge (Gilson) for 20 seconds and the clear fraction assayed. The assay was performed by loading 50 ml of the fraction automatically onto a Shimadzu LC6A HPLC and chromatographing on a TSK gel permeation column at a flow rate of 1 ml minute$^{-1}$ using sodium phosphate buffer (pH 7.0).

The peak heights representing the HA monomer were recorded and used to determine the concentration of monomer using a standard curve between 1 and 10 mgml$^{-1}$ monomeric HA.

The %-free monomeric HA was calculated by measuring the monomer concentration in the fixed microcapsules and representing this figure as a percentage of the monomer concentration of the unfixed microcapsules.

Heating of the spray dried microcapsules in an oven (as described in Example 1) results in a decrease in the amount of monomer that can be detected. This decrease in detectable monomeric HA is due to the denaturation and crosslinking of monomeric HA into insoluble polymers that cannot be assayed by the aforementioned HPLC method.

Using the HPLC method to assess HA monitor levels, it is clear that after 15 minutes incubation there is no free monomeric HA present in the HA microcapsules. However it is still possible to further crosslink the HA microcapsules by heating for longer periods.

This prolonged heating results in an increased level of microcapsule crosslinking which in turn produces microcapsules of increasing strength which are correspondingly more resistant to pressure.

By careful control of temperature and time of incubation, it is possible to produce microcapsules with a controlled range of crosslinking (and hence pressure resistivity).

EXAMPLE 4

MICROCAPSULE CLASSIFICATION

An advantage of the process of the invention is that it enables the median size and size distribution of the microcapsules to be controlled. However, one can further select desired sizes if one wishes, for example by flotation. In a homogeneous dispersion of microcapsules, larger particles will rise to the surface faster than smaller particles due to the lower density (more encapsulated air) of the larger particles. Hence, by allowing the dispersion to stand, the particle size distribution will change at any level of the solution with respect to time.

Microcapsules were dispersed in 2000 ml of aqueous solution containing 6% w/v sodium chloride and 0.1% w/v Pluronic F68 (™) in a glass bottle giving a liquid column of approximately 165 mm. A sampling tube was placed 50 mm below the upper liquid surface to enable removal of samples at timed intervals.

By altering the standing time and sodium chloride concentration, it was possible to produce a variety of particle size distributions and classify microcapsules down to 2 μm.

Other wet techniques for classification include hydrodynamic chromatography and field flow fractionation. 'Dry' techniques using the principles of elutriation and cross flow separation are commercially available in the form of the Microsplit (British Rem.), Zig-zag (Alpine) and Turbo (Nissuin) classifiers.

EXAMPLE 5

CHARACTERISATION OF HUMAN SERUM ALBUMIN MICROCAPSULE

The hollow microcapsules produced by the method of the invention have been found to be such that the amount of wall forming material used in production is considerably less than that used in previous production methods due to smaller mean size and improvements in the shell characteristics. However, despite this the echogenicity of the microcapsules is superior to that produced previously. This novel characteristic is measured and expressed as decibels (dB) of echogenicity per microgram/ml of albumin. Echogenicity can be defined as the ability of a material to reflect or "backscatter" ultrasound waves. The intensity of the backscatter is quantified by image analysis in terms of decibels. The greater the intensity of the signal, the more echogenic the sample.

All water used for the assay was pyrogen free and drawn two days before use, allowing it to degas by exposure to air.

To a 400 ml polypropylene test beaker (Fisons Scientific Equipment, UK), 350 ml of water was added and any air-bubbles allowed to float to the surface before use.

A Hewlett Packard Sonos 1000 ultrasound machine was used and the controls were set as follows: TGC (total gain control) #1, #2, #3, #4, #5, #6, #7, all =128; Compress=128 dB; and Transmit=60 dB. A 3.5 MHz transducer was used at a depth setting of 8 cm.

The transducer was introduced to the water to a depth of 1.5 cm and the magnetic follower set at 75 rotations/minute. A background recording of the backscatter intensity was initially made. An image analyser (Seescan, Cambridge, UK) was used to record the ultrasound scan for 1.2 seconds and then divide the recording into 10 individual time frames. Each frame was analysed for backscatter intensity and the statistical results calculated.

A homogeneous volume of suspended microcapsules was carefully added avoiding the introduction of air bubbles. The volume added was such that after administration, the microcapsule concentration within the ultrasound test cell was $1\times10^6$/ml. The microcapsules were allowed to disperse evenly throughout the water before a real time ultrasound scan was "captured" using the image analyser and the backscatter intensity measured.

The ultrasound instrument was calibrated by reference to a stainless steel reflector and a series of increasing echoreflective tissue mimicking silicone rubber blocks supplied by ATS Laboratories Inc. Bridgeport. Conn. 06608. USA. A calibration curve was drawn and subsequent measurements of Video Display Units, determined below, converted back to dB from the calibration curve produced. The assay was repeated three times and the average intensity measurement calculated.

The protein content of the human serum albumin microcapsules was determined using a modified Kjeldahl assay. The assay determines the nitrogen content of a sample of microcapsules which is then calculated in terms of the total protein concentration; from this result the protein of a fixed dumber of microcapsules and in particularly the protein content of the sample added to the echogenicity assay can be calculated.

The microcapsules were digested using a Tecator Digestion System 12 with any carbohydrate present in the sample being oxidised by hydrogen peroxide. Any protein, and thus the nitrogen present, is converted during the digestion to ammonium sulphate. This in turn is converted to ammonia by steam distillation under alkaline conditions. The liberated ammonia is condensed, absorbed into boric acid and the amount absorbed determined by titration with hydrochloric acid. This procedure was automated using a Kjeltec Auto 1030 analyser. Using appropriate standards the amount of protein present in a sample can be calculated.

From the total protein analysis, the amount of protein added to the echogenicity test cell was determined. The number of microcapsules administered was calculated as a weight of protein added and therefore the echogenicity per microgram/ml of microcapsules determined.

TABLE 2

Echogenicity Versus Weight of Microcapsules

| Batch No | Echogenicity (VDU) | Concn of Microcapsules Added (µg/ml) | Total VDU µg/ml microcapsules |
| --- | --- | --- | --- |
| AIP101/941 | 26 | 13.23 | 1.97 |
| AIP101/942 | 26 | 12.29 | 2.11 |
| AIP101/943 | 25 | 13.80 | 1.92 |
| AIP101/944 | 26 | 12.47 | 2.09 |
| Mean Result | — | — | 2.023 ± 0.09 |

| Batch No | Echogenicity (dB) | Wt of Microcapsules Added (µg/ml) | dB/µg/ml microcapsules |
| --- | --- | --- | --- |
| AIP101/941 | −7.4 | 13.23 | −0.56 |
| AIP101/942 | −7.4 | 12.29 | −0.6 |
| AIP101/943 | −7.3 | 13.80 | −0.53 |
| AIP101/944 | −7.4 | 12.47 | −0.59 |
| Mean Result | — | — | 0.57 ± 0.04 |

EXAMPLE 6

OPTIMISATION OF SPRAY DRYING CONDITIONS TO MAXIMISE THE NUMBER OF INTACT GAS-CONTAINING PARTICLES

We describe above the production of smooth, spherical and hollow microparticles for use in echocontrast imaging. It is desirable to minimise the number of particles larger than 6 µm and to maximise the number of gas-containing hollow particles. A series of experiments were performed under the conditions described in Example 1 to examine the influence of liquid feed rate on the yield of intact spherical particles. We found that increasing the liquid feed rate decreased the number of intact microparticles formed during the initial spray drying (Table 4). The mean particle size and overall pressure stability, ie thickness of the shell, do not change but the total echogenicity does, as the liquid flow rate is increased from 4 to 16 ml/min. We find that slower rates of evaporation (at higher liquid flow rates) lead to fewer intact gas-containing particles being formed.

TABLE 4

| Flow rates (ml/min) | 4 | 8 | 12 | 16 |
| --- | --- | --- | --- | --- |
| Mean size (µm) | 3.08 | 3.04 | 3.13 | 3.07 |
| Echogenicity (video density units) | 22 | 21 | 14 | 10 |
| Echogenicity after pressure (video density units) | 20 | 18 | 10 | 8 |

We claim:

1. A process for forming microcapsules comprising (i) providing a solution of a material in an aqueous solvent and (ii) spraying said solution into a gas such that said aqueous solvent evaporates, thereby forming hollow microcapsules, characterised in that the aqueous solution contains a liquid of greater volatility than water, wherein said liquid of greater volatility than water is a solvent for said material and is miscible with water.

2. A process according to claim 1 wherein the volatile liquid has a boiling point lying between 20° C. and 100° C. at atmospheric pressure.

3. A process according to claim 1 wherein the volatile liquid is ethanol or methanol.

4. A process according to claim 1 wherein the volatile liquid constitutes 0.1–80.0% v/v of the aqueous solution.

5. A process according to claim 4 wherein the volatile liquid constitutes 5.0–30.0% v/v of the aqueous solution.

6. A process according to claim 1 wherein the material is a protein.

7. A process according to claim 6 wherein the protein is albumin, collagen or gelatin.

8. A process according to claim 7 wherein the protein is albumin.

9. A process according to claim 1 wherein the material concentration in the solution is 1.0–25.0% w/v.

10. A process according to claim 1 wherein the solution additionally comprises a contrast agent selected from the group consisting of an X-ray contrast agent and magnetic resonance imaging contrast agent.

11. A process according to claim 1 wherein the microcapsules are subjected to heat treatment to further insolubilize the microcapsules.

12. A process according to any one of the preceding claims wherein the process is so carried out as to yield a sterile, intravenously injectable product.

13. A process according to claim 1, wherein said microcapsules are not subsequently freeze-dried.

14. A process according to any one of claims 1–9 or 10 wherein the microcapsules are subjected to radiation in order to sterilise the microcapsules.

* * * * *